United States Patent [19]

Watts

[11] 4,097,405
[45] Jun. 27, 1978

[54] PARTICULATE THICKENING AGENT

[75] Inventor: Ronald E. Watts, Harlow, England

[73] Assignee: Minnesota Mining and Manufacturing Company, Saint Paul, Minn.

[21] Appl. No.: 703,363

[22] Filed: Jul. 8, 1976

[30] Foreign Application Priority Data

Jul. 14, 1975 United Kingdom ............... 29490/75

[51] Int. Cl.$^2$ .......................... B01J 13/00; C08K 3/36
[52] U.S. Cl. ............................... 252/316; 260/29.6 H; 260/42.52; 260/42.55
[58] Field of Search ....................... 252/36; 260/42.52, 260/42.55, 29.6 H

[56] References Cited

U.S. PATENT DOCUMENTS

| | | | |
|---|---|---|---|
| 3,061,577 | 10/1962 | Pruett | 260/42.52 |
| 3,131,148 | 4/1964 | Taulli | 252/316 |
| 3,287,290 | 11/1966 | Bray | 260/42 |
| 3,679,382 | 7/1972 | Cohrs et al. | 252/316 |
| 3,962,267 | 6/1976 | Suzuki et al. | 260/42.43 |

*Primary Examiner*—James H. Derrington
*Attorney, Agent, or Firm*—Cruzan Alexander; Donald M. Sell; Mark A. Litman

[57] ABSTRACT

An effective thickening agent comprises particulate matter of less than 425 microns when said particulate matter comprises silica particles bonded to an acrylic polymer capable of hydrogen bonding.

10 Claims, No Drawings

PARTICULATE THICKENING AGENT

This invention relates to thickeners and in particular thickeners which can be provided in a dry solid form and which will readily disperse in liquids such as aqueous or polar liquids, to thicken them particularly when the liquids have neutral or alkaline pH values.

Many thickeners are known for addition to aqueous liquids but they have various disadvantages, particularly in that some cannot readily be dispersed in aqueous liquids and others cannot readily be supplied in a dry powder form for later dispersion into an aqueous liquid.

According to the invention there is provided a finely divided dry powder thickener comprising a finely divided silica which has a large surface area and which is itself capable of aggregating because of hydrogen bonding when dispersed in a liquid, and bonded to the silica a dried aqueous acrylic polymer latex, the acrylic polymer itself being capable of thickening and having some hydrophilic groups and other groups which are capable of forming hydrogen bonds with the silica, and the polymer being in a form which is readily dispersible in water or other aqueous liquids.

Such a thickener will very effectively thicken polar liquid compositions, e.g. water-based compositions, and has the important advantage that, after it has been dried and powdered, it can readily be dispersed in water-based compositions to thicken them. The thickners of the invention can therefore usefully be incorporated into dry solids powder compositions which have later to be dispersed or dissolved in water or other polar solvents. They can, for example, usefully be incorporated into hair bleaching compositions. The thickener of the invention also has the advantage that it will thicken polar liquid compositions which have a high content of dissolved solids.

It is believed that the silica particles should be in the form of spheroids with a relatively smooth surface and little or no internal porosity. The silica preferably has an average particle size of no more than 6 $\mu$, the practical lower limit of particle sizes being about 0.007 $\mu$, while the preferred particle size is about 0.01 $\mu$. The silica particles apparently form a thixotropic system when dispersed in water because of hydrogen bonding between the particles. Such silica particles can be made by high temperature hydrolysis of silicon tetrachloride and particles made in this way are commercially available under the tradename Cab-0-Sil from the Cabot Corporation. Other suitable silica particles are available under the tradename Santocel from Monsanto.

One preferred group of polymers are acrylic polymers which have some hydrophilic groups such as carboxylic groups to make the polymers readily dispersible in water and esters or like groups which will hydrogen bond with the silica particles. These acrylic polymers when in the form of an aqueous latex are themselves thickeners of aqueous systems forming a milky latex with water at acid pH values and a clear gel with water at neutral or alkaline pH values. The acrylic polymer latex is desirably one which contains some free carboxyl groups. A group of useful latices are those which are sold by Rohm and Haas under the name Acrysol. An example of these latices which we have found to be effective is referred to by the makers as ASE-95 and is described by them as an acrylic emulsion copolymer. This readily dissolves or disperses to form a clear highly viscous system in an alkaline solution. Acrysol ASE-95 is believed to be a 20% aqueous suspension of a linear copolymer of methacrylic acid and acrylic and methacrylic acid esters with a molecular weight of several million. On neutralizing with alkali it exhibits an equivalent weight of 123.5. At a pH of about 3.0 the suspension is milky and on addition of alkali the milkiness is gradually reduced until a clear viscous liquid is obtained when the pH is just greater than 7.0. Copolymers of at least one from the group methacrylic acid and acrylic acid, with at least one from the group lower alkyl acrylates and lower alkyl methacrylates (esp. methyl and ethyl) are desirable polymer materials for the latex.

When the thickener is to be brought to the dry powder form we have found that the finely divided silica and the acrylic polymer latex should be mixed and then the mixture dried and finely ground. Alternatively the mixture can be spray dried to give the fine particles. The resulting finely divided product is surprisingly readily dispersible provided it has a small particle size. The dried acrylic polymer latex without the silica is not, however, easily ground or redispersed. In addition this mixing before drying has the advantage of binding the silica particles which are otherwise so fine that they are readily blown about by air currents and also stick to glass and plastic surfaces because of electrostatic charges.

The resulting thickeners are finely divided (average size less than 425 $\mu$) particles comprised of silica and dried acrylic latex bonded together. When the silica and polymer are bonded together, the polymer must be in particulate — as opposed to film-form.

Of the mixture of silica and polymer, the latter desirably forms on a dry basis from 14 to 40%, and preferably about 24%, by weight of the mixture.

While both the finely divided silica and the acrylic polymer latex will separately give good thickening of an aqueous composition, the two together appear to exert a synergistic effect giving much better thickening after they have been mixed, dried together and then redispersed. This has the advantage that less total thickener can be used when the thickener is a mixture of the two components than when the single components are used on their own as a thickener. Also the bulk density of the dried thickener of the invention is relatively high as compared with the separate components and so the thickener of the invention has the advantage of requiring a smaller volume when packed as a dry powder as compared with the individual components.

After the thickeners have been dried to a low moisture content, for optimum results, they are finely ground to a particle size preferably below 150 $\mu$ or spray dried to give particles of a size preferably below 150 $\mu$. They can then readily be dispersed in water. It appears that a maximum particle size of 150 $\mu$ is highly desirable if the powder is to be readily redispersible to give a thickened liquid which quickly reaches its maximum viscosity and retains it for long periods of time. Thus with larger particle sizes the powder is much slower to redisperse and reach its required viscosity, and with larger particles the viscosity of the thickened liquid tends to increase with time as the larger particles gradually become redispersed.

The amount of residual water in the thickener powder appears to have some effect upon the properties of the thickener of the invention. We have found that best results are given when the dried mixture of silica and latex has a residual water content of about 2% by weight. A residual water content in the dried mixture as low as zero is possible although at such low residual water contents it is generally found that it is more difficult to redisperse the thickener in water. Higher residual water contents e.g. up to 16% by weight or higher are also possible with dry powder mixtures resulting, but with residual water contents which are too high the thickener tends to be sticky which is usually undesirable and might affect any water sensitive materials comixed with the thickener.

Water contents of 30% and more are useful where there are no additional ingredients which are water sensitive, and in the case of slow redispersible larger size particles, even higher water contents might be desirable.

The relative amount of water added to the thickener will determine the viscosity of the resulting composition and the relative proportions of thickener to water can vary widely, e.g. from 2.8 to 12.8 parts by weight of dry thickener per 100 parts by weight of water, since it appears that the effect of the thickener on the viscosity of the water or other compositions to which it is added is continuous from an imperceptible change for very small additions up to a self-supporting gel for large additions. Additionally, the pH of the thickened composition and the other components present will also markedly affect the resulting viscosity. In particular the thickeners of the invention tend to give increased viscosity at higher pH values, particularly neutral or alkaline values. These points can be demonstrated by the following tests in which the viscosities of various thickened active compositions were measured and the results shown in the following Table.

| Test Number | Composition | pH | Viscosity cP |
|---|---|---|---|
| A | 1.2 g Cab-O-Sil MS-7[+] | 4.0 | 210 |
|   | 15 g Water | 6.4 | 1,387.5 |
|   |   | 9.3 | 135.5 |
| B | 1.8 g Acrysol ASE-95[++] | 3.4 | 3.5 |
|   | 15 g Water | 5.9 | 19.7 |
|   |   | 9.6 | 13,750 |
| C | 1.5 g Thickener** | 3.5 | 3 |
|   | 17 g Water | 6.4 | 4,150 |
|   |   | 8.0 | 39,250 |
| D | 6 g Bleach powder* |   | No thickening |
|   | 17 g Water |   |   |
| E | 1.5 Thickener** | 9.13 | 13,050 |
|   | 6.0 g Bleach powder* |   |   |
|   | 17 g Water |   |   |
| F | 2 g Acrysol ASE-95[++] | 9.1 | 2,900 |
|   | 6 g Bleach powder* | 9.3 | 3,250 |
|   | 15 g Water |   |   |
| G | 1.25 g Cab-O-Sil MS-7[+] | 9.3 | 1,520 |
|   | 6.0 g Bleach powder* | 9.5 | 1,200 |
|   | 17 g Water |   |   |

*Composition of Bleach powder
sodium carbonate perhydrate 2.5 g,
sodium persulphate 2.5 g,
ammonium sulphate 0.5 g,
disodium EDTA 0.5 g.
[+]Cab-O-Sil MS-7 a finely divided silica having a particle size of 0.01 µ made by the high temperature hydrolysis of silicon tetrachloride and available from the Cabot Corporation.
[++]Acrysol ASE-95 an acrylic polymer latex available from Rohm and Haas.
**Thickener a mixture of 1.25 g of Cab-O-Sil MS-7 and 2.1 g (0.42 g dry) of Acrysol ASE-95, was dried and then an aliquot of 1.5 g of the dried mixture was redispersed in the water and used in the test.

As can be seen from these results, the thickener according to the invention (test C) gives very significant thickening at neutral and alkaline pH's, the degree of thickening increasing with pH value. Also by comparing tests C, D and E, the degree of thickening was reduced in the presence of the bleach powder but was still high, the bleach powders on their own giving no thickening.

The synergistic thickening effect of the thickener of the invention can readily be seen by comparing tests A, B and C. Thus the resulting viscosity using a thickener according to the invention is much greater than that expected from the use of the components alone. A similar effect can be seen by comparing tests E, F and G where the bleach powder was additionally present.

The preparation of thickeners according to the invention will now be illustrated by the following Examples.

EXAMPLE 1

Two ml of Acrysol ASE-95 (copolymer derived from 40% methacrylic acid and 30%/30% lower alkyl acrylates and methacrylates) were diluted with 6 ml of water and then stirred into 1.25 g of the silica, Cab-O-Sil MS-7, to form a smooth cream. The water was then removed to give a coarse granular material. This was then ground to pass a sieve with 150 $\mu$M apertures and was ready for use. If the dried mixture is not ground finely then the Acrysol dissolves slowly and thickening is obtained slowly.

EXAMPLE 2

A quantity of thickener was prepared as in Example 1 and ground and sieved to provide four fractions of the following particle sizes in microns: (A) 425 to 300, (B) 300 to 212, (C) 212 to 150, and (D) less than 150. Of each of these 1.5 g was mixed with 6 g of bleach powder as herein defined in connection with the Table and 17 ml of water was then stirred in.

One minute after adding the water, fraction D had thickened sufficiently not to drip from a swatch of hair held vertically. Fractions C, B and A were progressively less thick in that order and fraction A had scarcely thickened at all. After a further two minutes the viscosity of fraction D had increased slightly and then remained constant whilst the viscosity of the others continued to increase slowly. Even after one and a quarter hours there was still an obvious gradation through the series of viscosities of the fractions from D the thickest to A the thinnest and it was found that the bleach mixture containing fraction A dripped slowly from a swatch of hair held vertically.

It appears therefore that to achieve a constant viscosity fairly quickly after mixing with water, the thickener of the invention should not have a particle size greater than about 150 $\mu$.

What is claimed is:

1. A thickener comprising particulate matter of less than 425 microns, said particulate matter comprising silica particles of from $7 \times 10^{-3}$ to 6 $\mu$ bonded to an acrylic polymeric material comprising on a dry basis, from 14 to 40% by weight of said particulate matter and capable of hydrogen bonding and being sufficiently hydrophilic to be dispersible in water or other aqueous liquids, said silica having a large surface area and being capable of aggregating because of hydrogen bonding when dispersed in water.

2. The thickener of claim 1 which is further characterized by being a dry powder with less than 16% by weight water content.

3. A thickener comprising particulate matter of less than 425 microns, said particulate matter comprising silica particles of from $7 \times 10^{-3}$ to 6 $\mu$ bonded to an acrylic polymeric material which (1) comprises on a dry basis, from 14 to 40% by weight of said particulate matter, (2) is capable of hydrogen bonding, and (3) being sufficiently hydrophilic to be dispersible in water, said silica having a large surface area and being capable of aggregating because of hydrogen bonding when dispersed in water, said acrylic polymeric material comprising a copolymer of at least one acid selected from the group consisting of acrylic and methacrylic acid with at least one comonomer selected from the group consisting of lower alkyl acrylates and lower alkyl methacrylates.

4. The thickener of claim 3 wherein said lower alkyl acrylates and methacrylates are selected from the group consisting of methyl and ethyl acrylates and methacrylates.

5. The thickener of claim 3 which is further characterized by being a dry powder with less than 16% by weight water content.

6. The thickener of claim 4 which is further characterized by being a dry powder with less than 16% by weight water content.

7. The thickener of claim 3 in which the average particle size of said particulate matter is less than 150 microns.

8. The thickener of claim 4 in which the average particle size of said particulate matter is less than 150 microns.

9. The thickener of claim 3 in which said silica particles and said acrylic polymeric material were codried, said acrylic polymeric material being derived from an aqueous latex.

10. The thickener of claim 4 in which said silica particles and said acrylic polymeric material were codried, said acrylic polymeric material being derived from an aqueous latex.

* * * * *